United States Patent [19]

Wolff

[11] Patent Number: 5,418,123
[45] Date of Patent: May 23, 1995

[54] COLOR PHOTOGRAPHIC RECORDING MATERIAL CONTAINING A COLOR COUPLER OF THE PYRAZOLOAZOLE SERIES

[75] Inventor: Erich Wolff, Solingen, Germany

[73] Assignee: Bayer Aktiengesellschaft, Leverkusen, Germany

[21] Appl. No.: 151,010

[22] Filed: Nov. 12, 1993

[30] Foreign Application Priority Data

Nov. 27, 1992 [DE] Germany .................. 42 40 000.7

[51] Int. Cl.$^6$ ................................. G03C 7/38
[52] U.S. Cl. .................... 430/558; 430/386; 430/387
[58] Field of Search ............... 430/558, 386, 387

[56] References Cited

U.S. PATENT DOCUMENTS 5,270,156 12/1993 Hirabayashi et al. ............ 430/558

FOREIGN PATENT DOCUMENTS 489333 11/1991 European Pat. Off. .
3024256 1/1988 Japan .................................. 430/558

*Primary Examiner*—Lee C. Wright
*Attorney, Agent, or Firm*—Connolly and Hutz

[57] ABSTRACT

(Magenta) colour images with improved stability to light may be obtained with a colour photographic recording material containing compounds of formula I as magenta couplers. The magenta couplers of formula I are particularly suitable for use in recording materials of positive colour images on light reflecting or transparent supports.

10 Claims, No Drawings

COLOR PHOTOGRAPHIC RECORDING MATERIAL CONTAINING A COLOR COUPLER OF THE PYRAZOLOAZOLE SERIES

This invention relates to a colour photographic recording material containing at least one silver halide emulsion layer and a colour coupler of the pyrazoloazole series which enables magenta dye images with improved stability to light to be produced due to the presence of a special group.

It is known to produce colour photographic images by chromogenic development, i.e. by developing imagewise exposed silver halide emulsion layers with suitable colour developer substances, in the so called colour developers, presence of suitable colour couplers, the oxidation product of developer substances produced in correspondence with the silver image reacting with the colour coupler to form a dye image. The colour developers used are normally aromatic compounds containing primary amino groups, particularly those of the p-phenylenediamine series.

Pyrazolone couplers are normally used for producing magenta dye images. The image dyes obtained from these pyrazolone couplers in many cases have an absorption which is not ideal. Particularly disturbing is the yellow side absorption which necessitates the use of masking couplers or the employment of other masking techniques for producing brilliant colours in the photographic image. A certain improvement in this respect has been achieved by using 3-anilinopyrazolone coupler but the colour reproduction is still not quite satisfactory.

Magenta coupler of the pyrazoloazole series have proved to be particularly advantageous in this respect. They generally give rise to magenta dye images with a pure colour. Magenta couplers of this type are described, for example, in DE-A-I 810 462, DE-A 35 16 996, EP-A-0 143 570 and EP-A-0 176 804. One disadvantage of magenta couplers of the pyrazoloazole series in that the magenta dyes produced from them are frequently not sufficiently stable to the action of light.

Various factors are responsible for the stability to light of magenta azomethine dyes.

Thus for CN images viewed by reflected light ("paper images"), the image dyes obtained with colour developer CD-3 are preferably used; these are distinguished from the corresponding CD-4 derivates by significantly better stability in the light and dark.

The structure of the ballast group also plays an important part. Thus anilinopyrazolones which carry a stabilizer group derived from tertiary butyl hydroquinone have for many years been used as magenta couplers, e.g.

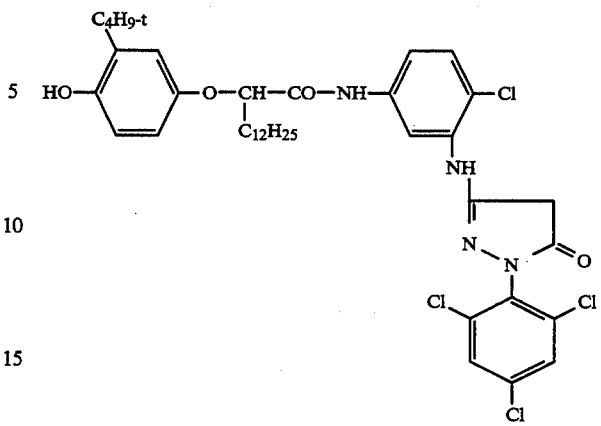

The corresponding hydroquinone diethers are also distinguished by good stability in the light (see DE-A-23 25 461). In recent times, however, special interest has been directed to a new class of magenta couplers, the pyrazoloazole couplers, which give rise to brilliant magenta dyes due to the absence of side absorption. These pyrazoloazole couplers can also be substantially improved In their stability to light by means of suitable stabilizer groups as described in EP-A-0 489 333, EP-A-0 482 081, JP 63-24256, JP 63-103244 or DE-A-29 21 778. Characteristic of all these compounds is that they have a connecting link between the pyrazoloazole portion which forms the chromophoto and the stabilizer group.

It has now been found that this connecting link is of decisive importance in pyrazolo[3,2-c]-1,2,4-triazole couplers for the stability of the dye to light.

Connecting links -L- which consist entirely of a chain of carbon atoms and connecting links -L- consisting entirely of a chain of carbon atoms and oxygen atoms have proved to be particularly suitable.

This invention relates to a colour photographic recording material containing at least one silver halide emulsion layer arranged on a layer support and at least one nondiffusible magenta coupler of the pyrazolo[3,2-c]-1,2,4-triazole series, characterised in that the magenta coupler corresponds to the following general formula I

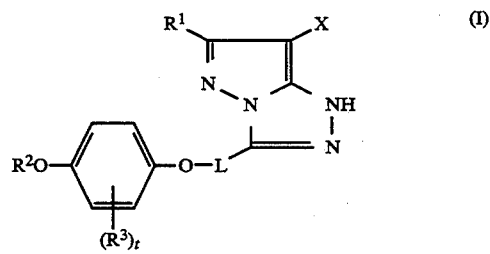

wherein
$R^1$ denotes alkyl;
$R^2$ denotes an alkyl group optionally substituted by OH, alkoxy, COOH or aryl;
$R^3$ denotes alkyl or aryl;
t stands for 0 to 4; or $R^2$ and $R^3$ together form a group for completing a 5-, 6- or 7-membered, optionally substituted ring;
L denotes a straight chain or branched alkylene group optionally interrupted by O and X denotes H or a group which can be split off in the process of colour development.

An alkyl group denoted by $R^1$ may be, for example, methyl, ethyl, propyl, isopropyl, tertiary butyl, hexyl or dodecyl. Branching on the α-carbon atom of this alkyl group as in isopropyl or tertiary butyl is preferred.

An alkyl group denoted by $R^2$ or a group denoted by $R^2$ and $R^3$ which completes a ring may contain a total of, for example, up to 18 carbon atoms. Examples of an alkyl group denoted by $R^2$ are: Methyl ethyl butyl tertiary butyl pentyl, hexyl, dodecyl and benzyl (=phenyl substituted methyl).

Examples of alkyl groups denoted by $R^3$ are: Methyl, tertiary butyl, pentyl, hexyl or a group which completes a ring together with $R^2$. Where several groups denoted by $R^3$ are present, these are not necessarily identical.

An alkylene group denoted by L contains, for example, up to 20 carbon atoms of which, for example, up to 8 carbon atoms may be in the main chain between the coupler portion and the hydroquinone portion. Alkylene groups having at least 2 carbon atoms in the main chain between the coupler portion and the hydroquinone portion are preferred.

A removable group denoted by X may in particular be a group which imparts no colour to the coupler. This group is preferably a halogen atom, in particular chlorine, or a preferably cyclic group attached to the coupling portion by way of an oxygen atom, a sulphur atom or a nitrogen atom.

If the removable group is a cyclic group, it may be attached at the coupling position of the coupler molecule either directly by an atom which forms part of a ring, e.g. a nitrogen atom, or indirectly by way of an interposed linking member. Large numbers of such removable groups are known, e.g. as leaving groups of 2-equivalent magenta couplers.

Examples of removable groups which are attached via oxygen correspond to the formula $$O-R^4$$

wherein $R^4$ stands for an acyclic or cyclic organic group, e.g. alkyl, aryl, a heterocyclic group or acyl which may be derived, for example, from an organic carboxylic or sulphonic acid. In particularly preferred removable groups of this type, $R^4$ is an optionally substituted phenyl group.

Examples of removable groups attached via nitrogen are described in the following German Offenlegungsschriften (DE-A-):
25 36 191, 27 03 589, 28 13 522 and 33 39 201.

These groups are in many cases 5-membered heterocyclic rings which are attached at the coupling position of the magenta coupler by a ring nitrogen atom. The heterocyclic rings in many cases contain activating groups such as carbonyl or sulphonyl groups or double bonds adjacent to the nitrogen atom which provides the link to the coupler molecule.

A removable group which is attached at the coupling position of the coupler by a sulphur atom may be the residue of a diffusible carbocyclic or heterocyclic mercapto compound which may be capable of inhibiting the development of silver halide. Such inhibitor groups have frequently been described as removable groups attached at the coupling position of couplers, including magenta couplers, e.g. in U.S. Pat. No. 3,227,554.

| | $R^1$ | $R^2$ | $R^3$ | L | X |
|---|---|---|---|---|---|
| M-1 | —C₄H₉-t | —C₄H₉ | —C₄H₉-t | —(CH₂)₃— | Cl |
| M-2 | —CH₃ | —C₆H₁₃ | " | " | Cl |
| M-3 | —C₃H₇-i | " | " | " | Cl |
| M-4 | —C₄H₉-t | —C₄H₉ | " | " | H |
| M-5 | " | —C₅H₁₁ | H | " | —O—⟨C₆H₄⟩—CH₃ |
| M-6 | " | —C₁₂H₂₅ | H | " | —S—⟨C₆H₃(OCH₃)⟩—C₈H₁₇-t |
| M-7 | " | —C₄H₉ | —CH₃ | —(CH₂)₄— | Cl |
| M-8 | —CH₃ | " | —C₄H₉-t | —(CH₂)₃— | —S—C₁₂H₂₅ |
| M-9 | —C₄H₉-t | " | " | " | pyrazolyl |

-continued
| | | | | |
|---|---|---|---|---|
| M-10 | —C₄H₉-t | —C₃H₇ | —C₄H₉-t | —(CH₂)₃— 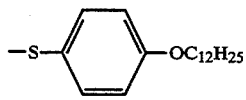 |
| M-11 | " | —C₂H₅ | " | —(CH₂)₆— 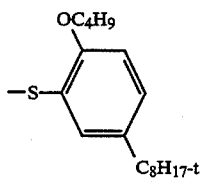 |
M-13
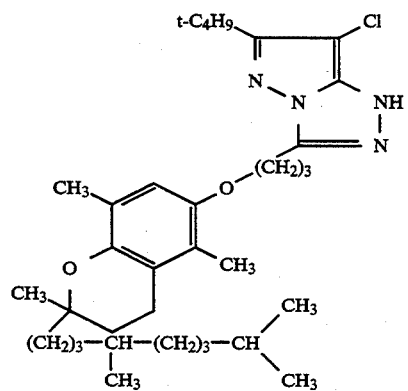
M-12
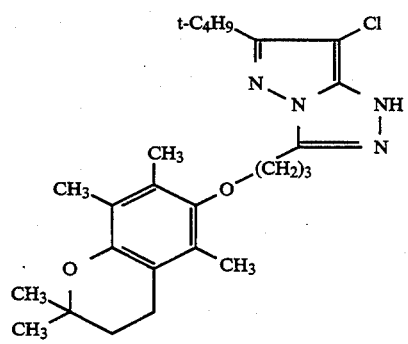
M-14
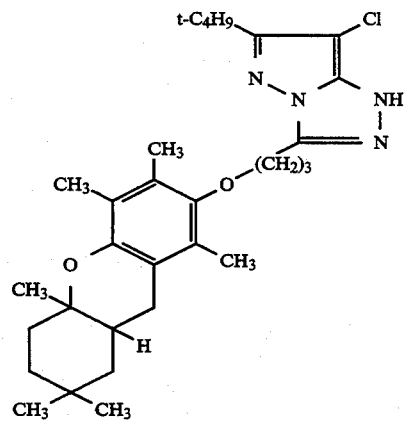
M-15

-continued
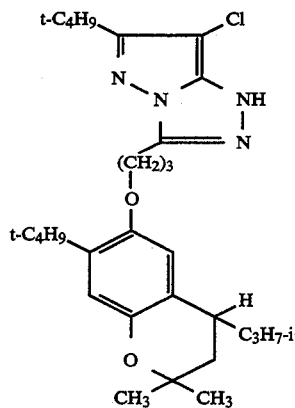
M-16
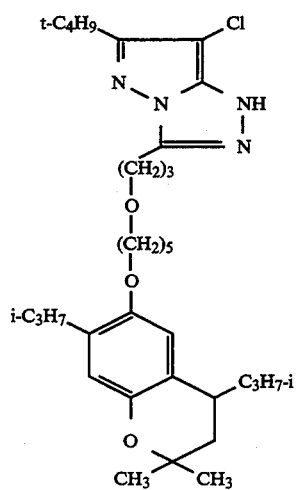
M-17
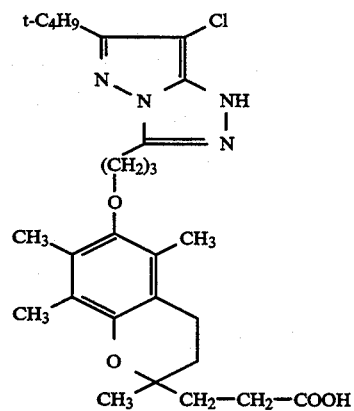
M-18

-continued
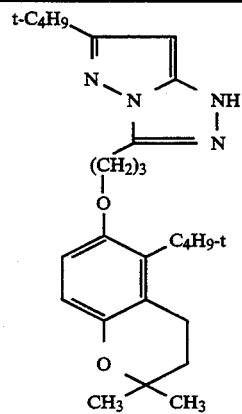
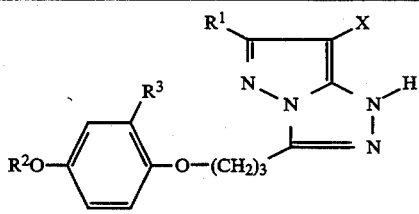
| | R¹ | R² | R³ | X |
|---|---|---|---|---|
| M-19 | —C₄H₉-t | —C₄H₉-t | —C₅H₁₁ | Cl |
| M-20 | " | " | —C₆H₁₃ | Cl |
| M-21 | " | H | —C₄H₉-t | Cl |
| M-22 | —CH₃ | H | " | —S—C₁₂H₂₅ |
| M-23 | —C₄H₉-t | —CH₃ | —CH₃ | H |
| M-24 | —C₃H₇-i | —C₁₂H₂₅ | —CH₃ | Cl |
| M-25 | —C₄H₉-t | —CH₂—C₆H₅ | H | Cl |
| M-26 | " | —C₆H₁₃ | —C₄H₉-t | Cl |
| M-27 | " | —C₅H₁₁ | " | —O—C₆H₄—OCH₃ |
| M-28 | " | —C₂H₅ | " | —S—(2-OC₄H₉, 5-C₈H₁₇-t)C₆H₃ |
M-29
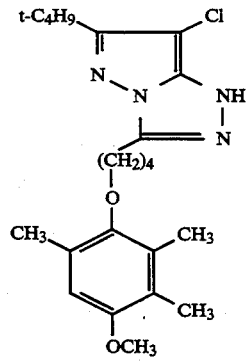
M-30

-continued
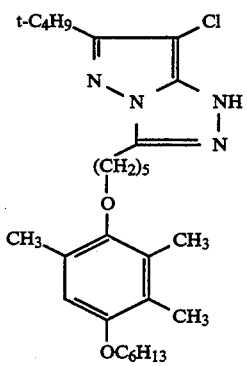
M-31
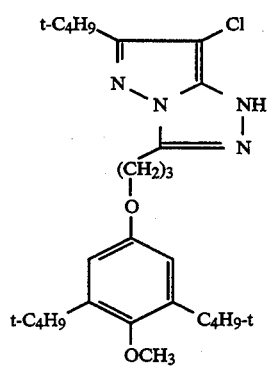
M-32
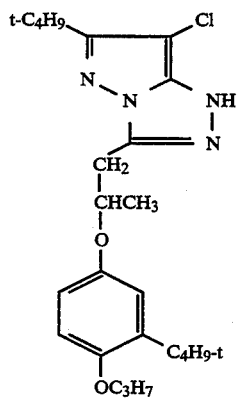
M-33
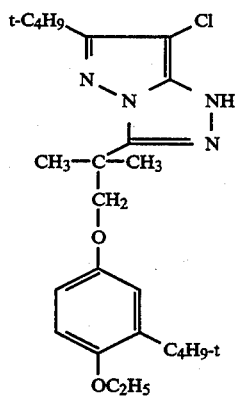
M-34

-continued
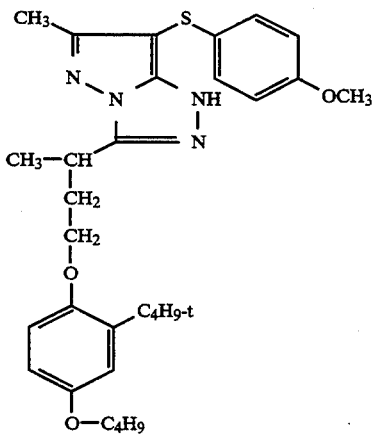
M-35
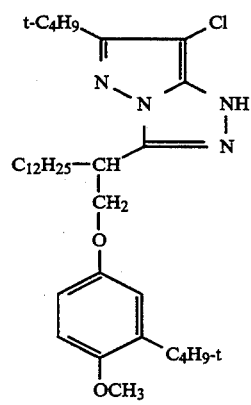
M-36
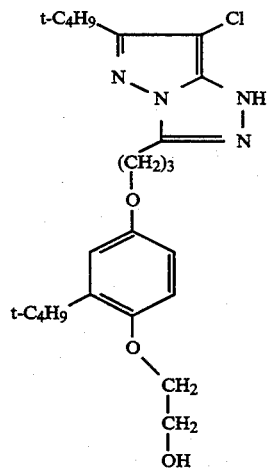
M-37

-continued
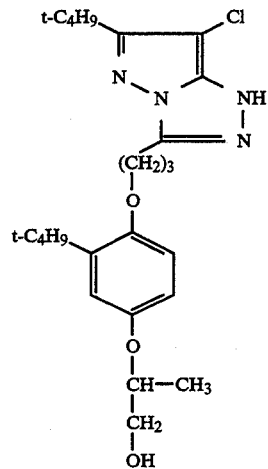
M-38
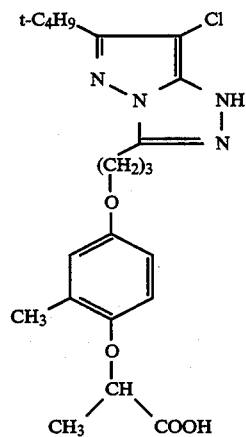
M-39
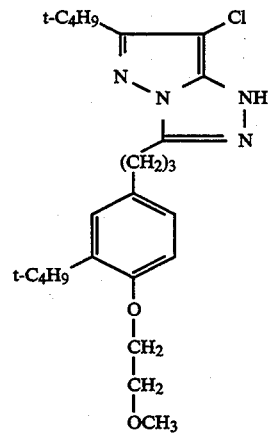
M-40

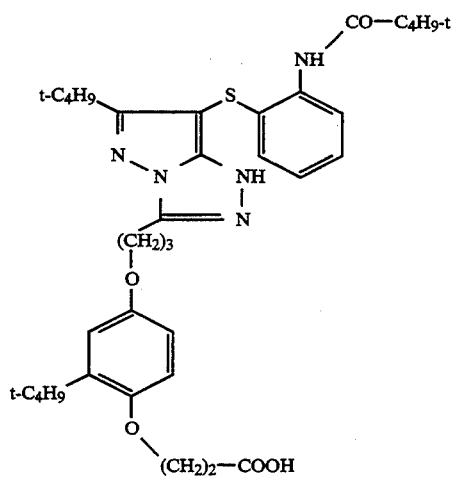
M-41
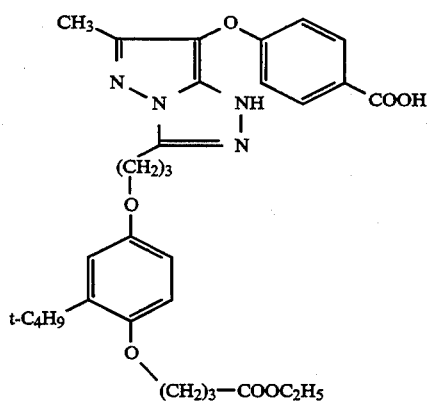
M-42
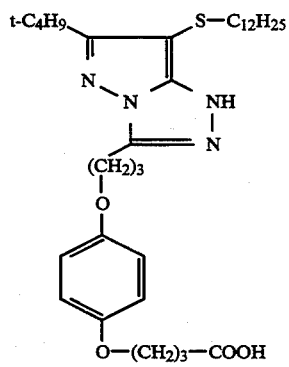
M-43

-continued
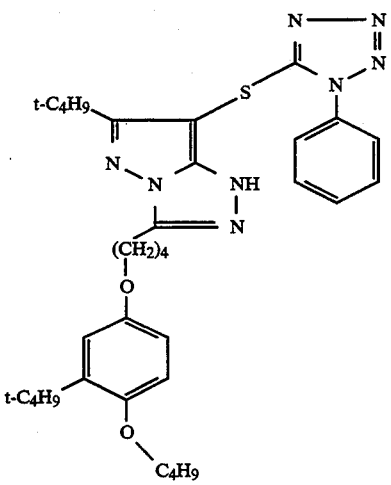
The various pyrazolotriazoles may be synthesized by many different methods; see:
e.g., 1. Bailey: Journ. Soc. Perk. I 1977, 2047 EP-A-0 284 240;
Research Disclosure 12 443, August 1974;
H.G.O. Becker and H. Böttcher: Journ. f. prakt. Chemie, 314, (1) 55 to 65 (1972);
EP-A-0 200 354, EP-A-0 178 788, EP-A-0 284 240;
J. Het. Chem. 16, 195 (1979);
EP-A-0 119 860.
The pyrazolo[2,3-c]-1,2,4-triazole ring system may, for example, be synthesized as follows:
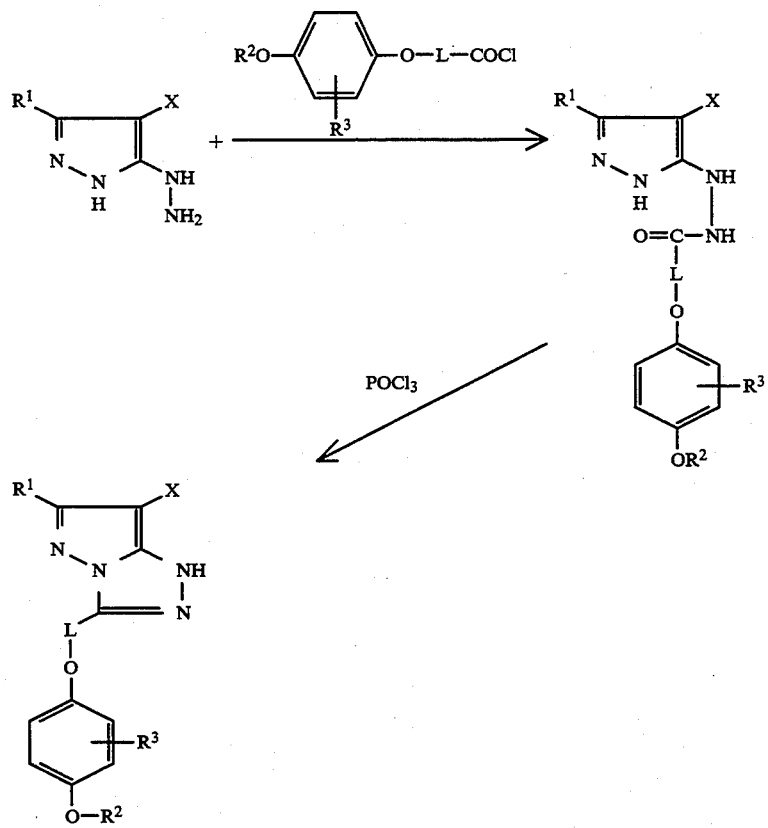

-continued
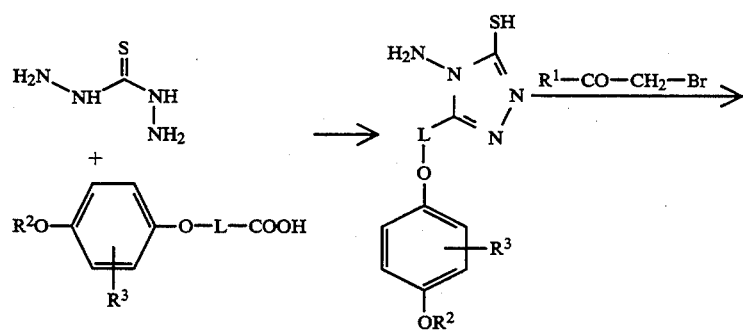
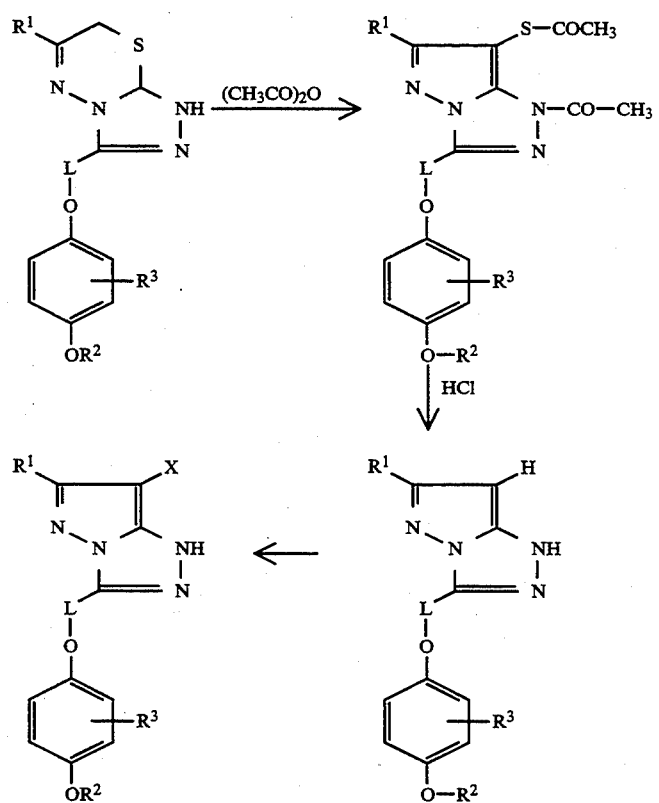
C. see Ann. 594, 14 (1955), J. Heterocycl. Chem. 11, 751 (1974)
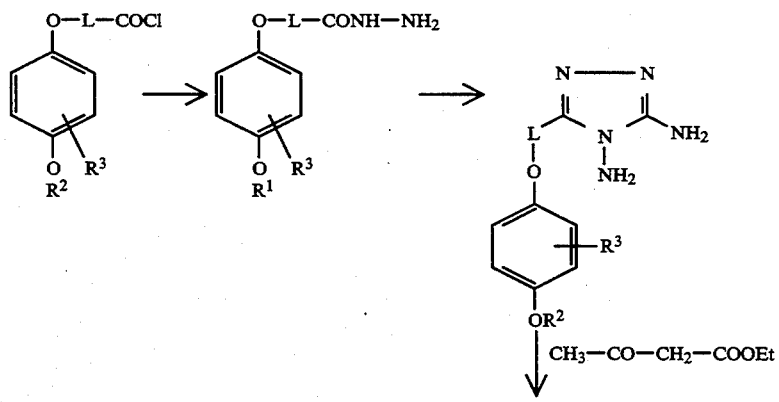

D. see EP-A-0 423 587

Compounds having a tertiary butyl group as substituent $R^3$ are particularly suitable. t-Butyl hydroquinone is available on a large technical scale as starting material for such compounds. Various methods of synthesis may be employed, depending on the position of this sterically demanding group:

a)

b)

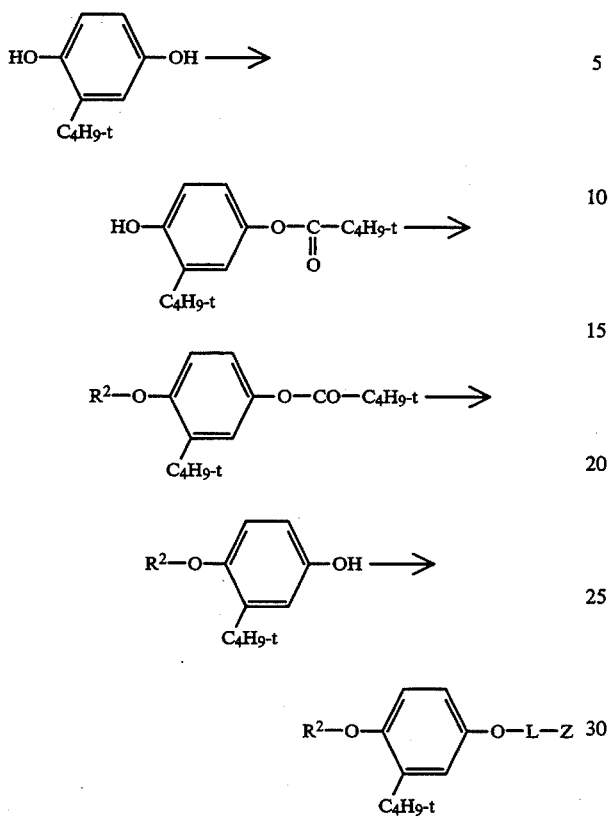

wherein Z in both cases stands for a functional group required for the pyrazolotriazole ring closure.

The principle of this second route b) has been fully described by Luke K.T. Tam and Kelly Farhat in Organic Preparations and Procedures INT. 10(2) 79–82 (1978).

Example of synthesis 1: M-1

| 1.1 | 213 g | of 2-t-butylhydroquinone are introduced into |
| | 1.3 l | of toluene under nitrogen. Distillation is then carried out until all traces of water have been displaced (removed). After the addition of |
| | 250 g | of 4-bromobutyric acid ethyl ester, |
| | 237 ml | of sodium methylate solution and a further |
| | 100 ml | of 4-bromobutyric acid ethyl ester and a further |
| | 100 ml | of sodium methylate solution are added dropwise within 4 hours. The reaction mixture is then stirred for 2 hours at boiling point and subsequently stirred into |
| | 5 l | of ice/HCl. After the addition of |
| | 2 l | of ethyl acetate, the reaction mixture is separated in a separating funnel and dried over calcium chloride and the solvent mixture is distilled off in a rotary evaporator. An oily residue of |
| | 262 g | of (4-hydroxy-3-t-butyl)4-phenoxybutyric acid ester remains behind. This consists of a mixture of methyl and ethyl ester. |
| 1.2 | 160 g | of the ester thus prepared are heated to boiling in |
| | 1300 ml | of acetone (p.a.) together with |
| | 230 g | of ground potash. After the addition of |
| | 3 g | of KI, |
| | 100 g | of n-bromobutane are slowly added dropwise and a further |
| | 100 g | of potash is introduced. An additional |
| | 3 × 30 g | of n-bromobutane is added during the reaction time of 72 hours. |
| | Yield: | 180 g of 4-(4'-n-butoxy-3-t-butyl)phenoxybutyric acid ester mixture. |
| 1.3 | 92 g | of the ester mixture thus obtained are dissolved in |
| | 350 ml | of ethanol and a solution of |
| | 35 ml | of water and |
| | 40 ml | of saturated sodium hydroxide is added. The reaction mixture is heated on a water bath for 30 minutes and then stirred into |
| | 2 l | of ice/HCl. The precipitate obtained is suction filtered, thoroughly washed with water and dried. After it has been stirred up with petroleum ether, it is again suction filtered and dried. |
| | Yield: | 72 g of 4(4'-n-butoxy-3-t-butyl)phenoxy butyric acid. |
| 1.4 | 48 g | of phosphorus pentachloride are added portionwise to |
| | 70 g | of the acid obtained under 1.3 in |
| | 400 ml | of ligroin. The reaction mixture is heated to 50° C. and then stirred for 1.5 hours and subsequently concentrated by evaporation in a rotary evaporator. |
| | Yield: | 77.5 g of 4(4'-n-butoxy-3-t-butyl)phenoxybutyric acid chloride. |
| 1.5 | 110 g | of Sodium acetate are dissolved in |
| | 600 ml | of water and the solution is cooled to a temperature of from 5 to 10° C. after the addition of 80 ml of ethyl acetate. |
| | 95 g | of 3-t-Butyl-4-chloro-5-hydrazinopyrazole are then introduced and |
| | 77 g | of 4(4'-n-butoxy-3-tert.-butyl)phenoxybutyric acid chloride in |
| | 300 ml | of ethyl acetate are added dropwise. The reaction mixture is then stirred for 30 minutes and after the residue has been separated it is washed twice with water and then with isopropylether. |
| | Yield: | 94 g |
| 1.6 | 94 g | of the product thus obtained are dissolved in |
| | 400 ml | of diglyme at 60° C. and |
| | 60 ml | of phosphorus oxychloride are added dropwise. During this addition, the temperature rises to 90–95° C. After completed reaction, the reaction product is stirred into water and the solid product is separated by suction filtration. The crude product thus obtained is recrystallised from methanol with the addition of Fullers earth and active charcoal. |
| | Yield: | 67 g of coupler M-1 Melting point: 141–143° C. |

Examples of colour photographic materials include in particular colour negative films, colour reversal films and colour photographic paper.

Suitable supports for the preparation of colour photographic materials are e.g. films and foils of semisynthetic and synthetic polymers such as cellulose nitrate, cellulose acetate, cellulose butyrate, polystyrene, polyvinyl chloride, polyethylene terephthalate and polycarbonate and paper laminated with a baryta layer or with a layer of α-olefin polymer (e.g. polyethylene). These supports may be coloured with dyes and pigments, for example titanium dioxide. The surface of the support is generally subjected to a treatment to improve the adhesiveness of the photographic emulsion layer, for example a corona discharge followed by the application of a subbing layer.

The colour photographic materials generally contain at least one red sensitive, at least one green sensitive and at least one blue sensitive silver halide emulsion layer and optionally interlayers and protective layers.

Binders, silver halide grains and colour couplers are essential components of the photographic emulsion layers.

The binder used is preferably gelatine but this may be partly or completely replaced by other synthetic, semi-synthetic or naturally occurring polymers. Examples of synthetic gelatine substitutes are: polyvinyl alcohol, poly-N-vinylpyrrolidone, polyacrylamides, polyacrylic acid and derivatives thereof, in particular their copolymers. Examples of naturally occurring gelatine substitutes include other proteins, such as albumin or casein, cellulose sugar starch and alginates.

Semi-synthetic gelatine substitutes are generally modified natural products. Cellulose derivatives such as hydroxyalkyl cellulose, carboxymethyl cellulose and phthalyl cellulose as well as gelatine derivatives obtained by a reaction with alkylating or acylating agents or by the grafting of polymerisable monomers are examples of these.

The binders should have a sufficient quantity of functional groups available so that sufficiently resistant layers can be produced by a reaction with suitable hardeners. Such functional groups are in particular amino groups but also carboxyl groups, hydroxyl groups and active methylene groups.

Gelatine, which is the binder preferably used, may be obtained by acid or alkaline decomposition. Oxidized gelatine may also be used. The preparation of such gelatines is described, for example, in The Science and Technology of Gelatine published by A.G. Ward and A. Courts, Academic Press 1977, page 295 et seq. Whichever gelatine is used, it should contain as little photographically active impurities as possible (inert gelatine). Gelatines which have a high viscosity and low tendency to swelling are particularly advantageous.

The silver halide present as light sensitive component in the photographic material may be a chloride, bromide or iodide or mixtures thereof. For example, the halide content of at least one layer may consist of from 0 to 15 mol-% of iodide, from 0 to 100 mol-% of chloride and from 0 to 100 mol-% of bromide. Silver iodobromide emulsions are generally used for colour negative and colour reversal films and silver chlorobromide emulsions with a high chloride content up to pure silver chloride emulsions are used for colour negative and colour reversal paper. The silver halides may be predominantly in the fore of compact crystals which may e.g. be in the form of regular cubes or octahedrons or transitional forms. On the other hand, he silver halide may also advantageously contain platelet shaped crystals having an average ratio of diameter to thickness of preferably at least 5:1, the diameter of a grain being defined as the diameter of a circle whose surface area is equal to the projected surface area of the grain. The layers may also contain tabular silver halide crystals in which the ratio of diameter to thickness is substantially greater than 5:1, e.g. from 12:1 to 30:1.

The silver halide grains may also have a multilayer grain structure, in the simplest case with an inner and an outer grain region (core/shell) in which the individual grain regions differ from one another in their halide composition and/or by other modifications, e.g. doping. The mean grain size of the emulsion is preferably from 0.2 μm to 2.0 μm and the grain size distribution may be either homodisperse or heterodisperse. A homodisperse grain distribution means that 95% of the grains differ by not more than ±30% from the mean grain size. The emulsions may contain organic silver salts in addition to silver halide, e.g. silver benzotriazolate or silver behenate.

Two or more types of silver halide emulsions which have been prepared separately may be used as a mixture.

The emulsions may be chemically or spectrally sensitized in the usual manner and the emulsion layers as well as other, light-insensitive layers may be hardened in the usual manner with known hardeners, in particular with carboxyl group-activating hardeners such as carbamoyl pyridinium salts (e.g. according to DE-A-22 25 230, DE-A-23 17 677 and DE-A-24 39 551).

Colour photographic silver halide materials normally contain at least one silver halide emulsion layer for each of the three spectral regions, red, green and blue. The photographic emulsions may be spectrally sensitized for this purpose with the aid of methine dyes or other dyes. Cyanine dyes, merocyanine dyes and complex merocyanine dyes are particularly suitable dyes.

A survey of polymethine dyes suitable as spectral sensitizers and suitable combinations thereof including supersensitizing combinations is given in Research Disclosure 17643 (December 1978), Chapter IV.

The following dyes in particular, are suitable, given in order of the spectral regions:

1. as red sensitizers
   9-Ethylcarbocyanines containing benzothiazole, benzoselenazole or napthothiazole as basic end groups which may be substituted in the 5- and/or 6- position by halogen, methyl, methoxy, carbalkoxy or aryl, and 9-ethyl-naphthoxathia- or -selenacarbocyanines and 9-ethyl-naphthothiaoxa- or benzimidazocarbocyanines, provided the dyes carry at least one sulphoalkyl group on the heterocyclic nitrogen.
2. as green sensitizers
   9-Ethylcarbocyanines containing benzoxazole, naphthoxazole or a benzoxazole and a benzothiazole as basic end groups, and benzimidazocarbocyanines which may be further substituted and must also contain at least one sulphoalkyl group on the heterocyclic nitrogen.
3. as blue sensitizers
   symmetric or asymmetric benzimidazo-, oxa-, thia- or selenacyanines having at least one sulphoalkyl group on the heterocyclic nitrogen and optionally further substituents on the aromatic nucleus, and apomerocyanines containing a rhodanine group.

Sensitizers may be omitted if the intrinsic sensitivity of the silver halide is sufficient for a particular spectral region, for example the blue sensitivity of silver bromides.

Non-diffusible low molecular or polymeric colour couplers are associated with the variously sensitized emulsion layers. These couplers may be present in the given sensitized emulsion layer or in an adjacent layer. Cyan couplers are generally associated with the red sensitive layers, magenta couplers with the green sensitive layers and yellow couplers with the blue sensitive layers.

Colour couplers for producing the cyan partial colour image are generally couplers of the phenol or α-naphthol series; the following are suitable examples:

(II)

[Structure: naphthol with OH, CONH—R³, R¹, R²]

C-1: R¹, R² = H; R³ = —(CH₂)₃—O—[phenyl with C₅H₁₁-t, C₅H₁₁-t]

C-2: R¹ = —NHCOOCH₂—CH(CH₃)₂; R² = H;
R³ = —(CH₂)₃—OC₁₂H₂₅

C-3: R¹ = H; R² = —OCH₂—CH₂—SO₂CH₃; R³ = —C₁₆H₃₃

C-4: R¹ = H; R² = —OCH₂—CONH—(CH₂)₂—OCH₃;
R³ = —(CH₂)₄—O—[phenyl with C₅H₁₁-t, C₅H₁₁-t]

C-5: R¹, R² = H; R³ = —(CH₂)₄—O—[phenyl with C₅H₁₁-t, C₅H₁₁-t]

C-6: R¹, R² = H; R³ = —(CH₂)₄—O—[phenyl with C₄H₉-t, H]

C-7: R¹ = H; R² = Cl; R³ = —C(C₂H₅)₂—C₂₁H₄₃

C-8: R¹ = H; R² = —O—CH₂—CH₂—S—CH(COOH)—C₁₂H₂₅
R³ = Cyclohexyl (III)

[Structure with two phenyl rings, OH, NHCONH, CONH, R¹, R², R³, R⁴, C₅H₁₁-t, t-C₅H₁₁]

C-9: R¹ = —C₄H₉; R² = H; R³ = —CN; R⁴ = Cl
C-10: R¹ = —C₄H₉; R² = H; R³ = H; R⁴ = —SO₂CHF₂
C-11: R¹ = —C₄H₉;
R² = —O—[phenyl]—C(CH₃)₂—CH₂—C(CH₃)₃;
R³ = H; R⁴ = —CN
C-12: R¹ = C₂H₅; R², R³ = H; R⁴ = —SO₂CH₃
C-13: R¹ = —C₄H₉; R², R³ = H; R⁴ = —SO₂—C₄H₉

C-14: R¹ = —C₄H₉; R² = H; R³ = —CN; R⁴ = —CN
C-15: R¹ = —C₄H₉; R², R³ = H; R⁴ = —SO₂—CH₂—CHF₂
C-16: R¹ = —C₂H₅; R², R³ = H; R⁴ = —SO₂CH₂—CHF—C₃H₇
C-17: R¹ = —C₄H₉; R², R³ = H; R⁴ = F
C-18: R¹ = —C₄H₉; R², R³ = H; R⁴ = —SO₂CH₃
C-19: R¹ = —C₄H₉; R², R³ = H; R⁴ = —CN (IV)

[Structure with OH, Cl, NHCO—CH—O—phenyl, R¹, R², R³, R⁴]

C-20: R¹ = —CH₃; R² = —C₂H₅; R³, R⁴ = —C₅H₁₁-t
C-21: R¹ = —CH₃2; R² = H; R³, R⁴ = —C₅H₁₁-t
C-22: R¹, R² = —C₂H₅; R³, R⁴ = —C₅H₁₁-t
C-23: R¹ = —C₂H₅; R² = —C₄H₉; R³, R⁴ = —C₅H₁₁-t
C-24: R¹ = —C₂H₅; R² = —C₄H₉; R³, R⁴ = —C₄H₉-t (V)

[Structure with R¹—phenyl—O—CH(R³)—CONH—phenyl with R², OH, NHCO—R⁵, R⁴]

C-25: R¹, R² = —C₅H₁₁-t; R³ = —C₄H₉; R⁴ = H; R⁵ = —C₃F₇
C-26: R¹ = —NHSO₂—C₄H₉; R² = H; R³ = —C₁₂H₂₅; R⁴ = Cl;
R⁵ = Phenyl
C-27: R¹, R² = —C₅H₁₁-t; R³ = —C₃H₇-i; R⁴ = Cl;
R⁵ = Pentafluorophenyl
C-28: R¹ = —C₅H₁₁-t; R² = Cl; R³ = —C₆H₁₃; R⁴ = Cl;
R⁵ = -2-chlorophenyl Phenolic cyan couplers which carry a ballasted acylamino group in the 2-position and an ethyl group in the 5-position are preferably used as cyan couplers in the recording material according to the invention, e.g. couplers of formula IV in which R¹ stands for ethyl and R², R³ and R⁴ for alkyl.

For producing the magenta partial colour image, the recording material of the present invention contains at east one magenta coupler corresponding to formula I, e.g. a magenta coupler of one of the formulae H-i to M-35.

Colour couplers for producing the yellow partial colour image are generally couplers containing an open chain ketomethylene group, in particular couplers of the α-acylacetamide series; suitable examples of these are α-benzoylacetanilide couplers and α-pivaloylacetanilide couplers corresponding to the following formulae:

(VI)

[Structure: R¹—CO—CH(R²)—CONH—phenyl with R³, R⁴, R⁵]

Y-1: R¹ = —C₄H₉-t;

R² = —N[ring with O, OC₂H₅, N—CH₂—phenyl, O]; R³ = Cl; R⁴ = H;

$R^5 = -NHCO-CH-O-$ 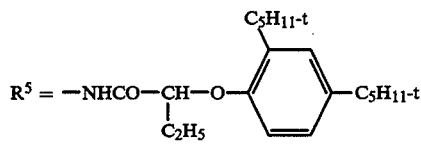
  　　　　　　　　　$|$
  　　　　　　　$C_2H_5$
Y-2: $R^1 = -C_4H_9\text{-}t$;
$R^2 = -N$ 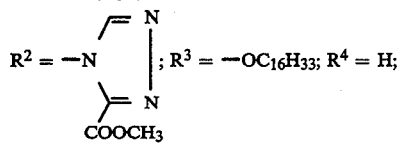 ; $R^3 = -OC_{16}H_{33}$; $R^4 = H$;
$R^5 = -SO_2NHCH_3$
Y-3: $R^1 = -C_4H_9\text{-}t$;
$R^2 = $ 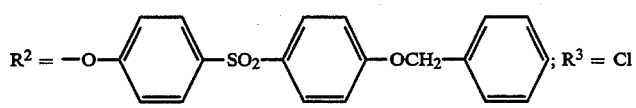 ; $R^3 = Cl$;
$R^4 = H$; $R^5 = -NHSO_2-C_{16}H_{33}$
Y-4: $R^1 = -C_4H_9\text{-}t$;
$R^2 = -N$ 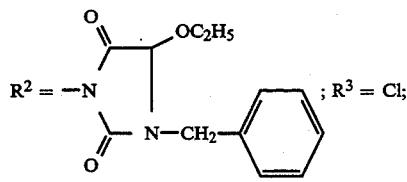 ; $R^3 = Cl$;
$R^4 = H$; $R^5 = -COOC_{12}H_{25}$
Y-5: $R^1 = -C_4H_9\text{-}t$;
$R^2 = $ 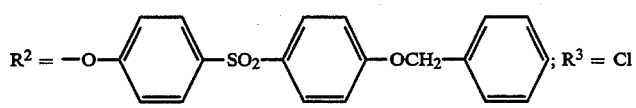 ; $R^3 = Cl$;
$R^4 = H$; $R^5 = $ 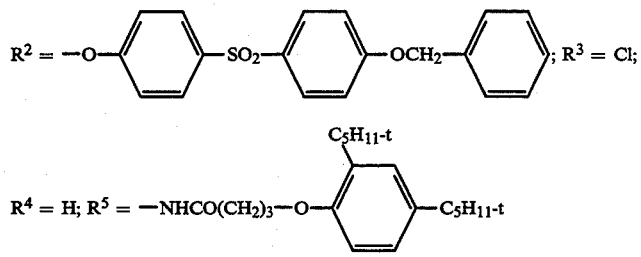
Y-6: $R^1 = -C_4H_9\text{-}t$;
$R^2 = $ 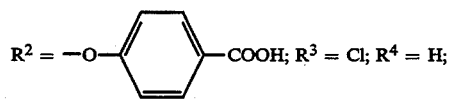 ; $R^3 = Cl$; $R^4 = H$;
$R^4 = H$; $R^5 = $ 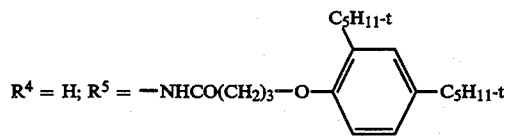
Y-7: $R^1 = -C_4H_9\text{-}t$;
$R^2 = $ 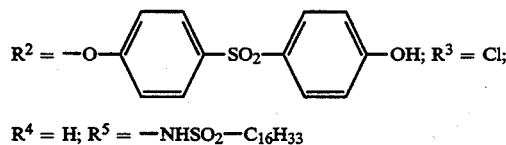 ; $R^3 = Cl$;
$R^4 = H$; $R^5 = -NHSO_2-C_{16}H_{33}$
Y-8: $R^1 = -C_4H_9\text{-}t$;

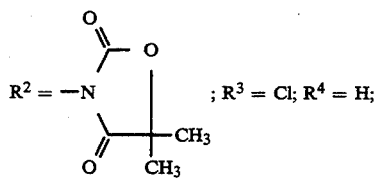
$R^3$ = Cl; $R^4$ = H;
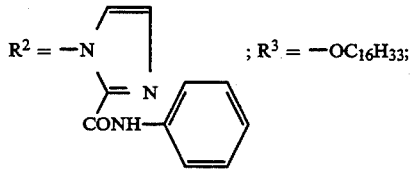
Y-9: $R^1$ = —$C_4H_9$-t;
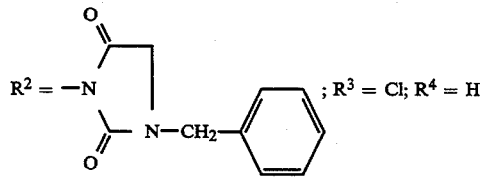
$R^3$ = —$OC_{16}H_{33}$;
$R^4$ = H; $R^5$ = —$SO_2NHCOC_2H_5$
Y-10: $R^1$ = —$C_4H_9$-t;
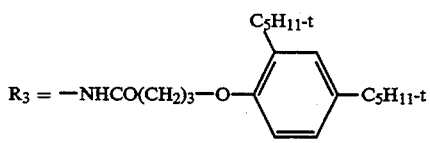
$R^3$ = Cl; $R^4$ = H
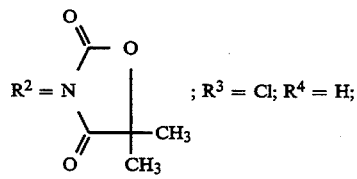
Y-11: $R^1$ = —$C_4H_9$-t;
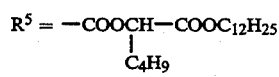
$R^3$ = Cl; $R^4$ = H;
$R^5$ = —COOCH—COO$C_{12}H_{25}$
      |
      $C_4H_9$
Y-12: $R^1$ = —$C_4H_9$-t;
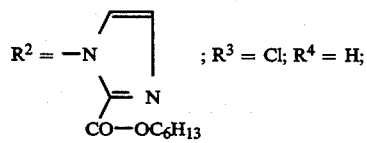
$R^3$ = Cl; $R^4$ = H;
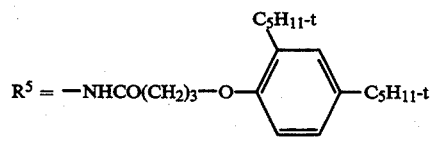
Y-13: $R^1$ = —$C_4H_9$-t;

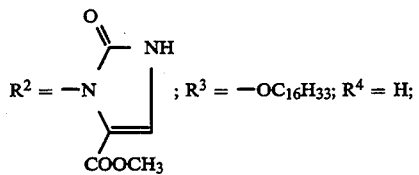
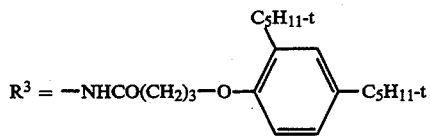
Y-14: $R^1 = -C_4H_9\text{-t}$;
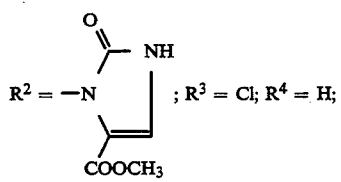
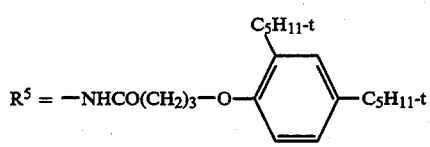
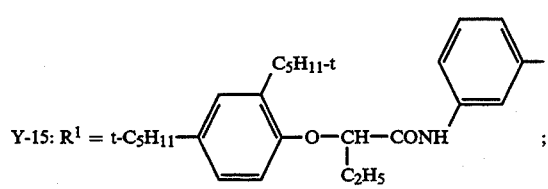
$R^2, R^4, R^5 = H; R^3 = -OCH_3$
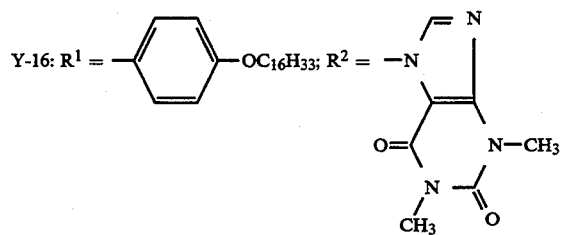
$R^3, R^5 = -OCH_3; R^4 = H$
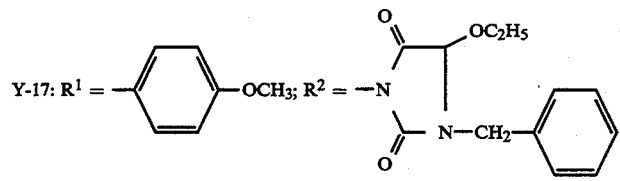
$R^3 = Cl; R^4 = H; R^5 = -COOC_{12}H_{25}$ Y-18: $R^1 =$ 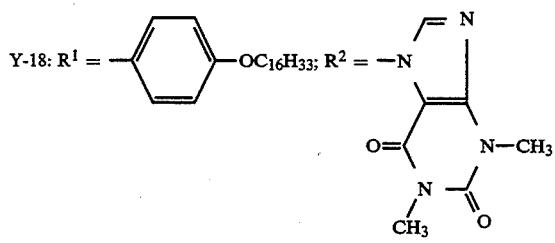

$R^3 = Cl; R^4, R^5 = -OCH_3$

Y-19: $R^1 =$ 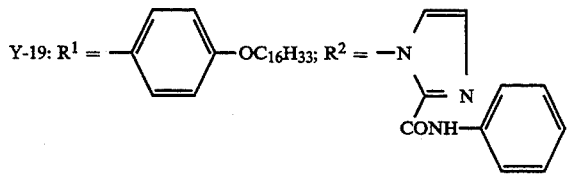

$R^3 = -OCH_3; R^4 = H; R^5 = -SO_2N(CH_3)_2$

Y-20: $R^1 =$ 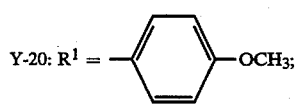

$R^2 =$ 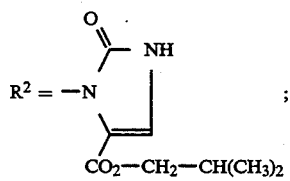 ;

$R^3 = -OCH_3; R^4 = H;$ $R_5 =$ 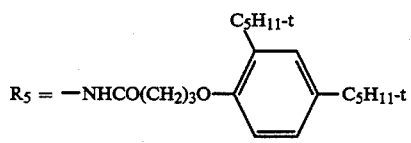

Y-21: 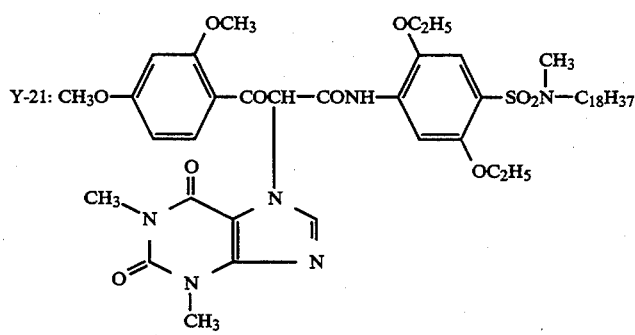

Pivaloyl acetanilide yellow couplers are the preferred yellow couplers for the recording material according to the invention, e.g. couplers corresponding to formula VI in which $R^1$ stands for tertiary butyl, $R^2$ for a fugitive group, $R^3$ for chloro or alkoxy, $R^4$ for H and $R^5$ for acylamino, sulphonamido, sulphamoyl or alkoxycarbonyl.

The colour couplers may be 4-equivalent couplers or 2-equivalent couplers. The latter are derived from 4-equivalent couplers in that they carry in the coupling position a substituent which is split off in the coupling reaction. 2-Equivalent couplers include couplers which are colourless as well as couplers which have an intense colour of their own which disappears in the process of colour coupling or is replaced by the colour of the image dye produced (masking couplers) and white couplers which give rise to substantially colourless products in the reaction with colour developer oxidation products. 2-Equivalent couplers also include couplers which carry, in the coupling position, a removable group which is released in the reaction with colour developer oxidation products and then develops a particular desirable photographic activity, e.g. as development inhibitor or accelerator, either directly or after one or more further groups have been split off from this originally released group (e.g. DE-A-27 03 145, DE-A-

28 55 697, DE-A-31 05 026, DE-A-33 19 428). The known DIR couplers as well as DAR and FAR couplers are examples of such 2-equivalent couplers.

The following are examples of white couplers:

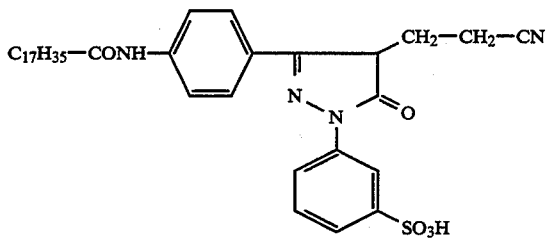

W-1

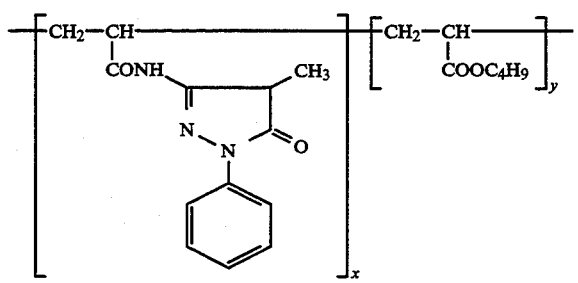

W-2

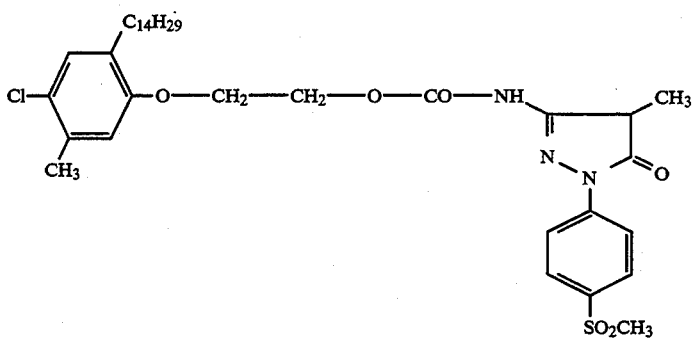

W-3

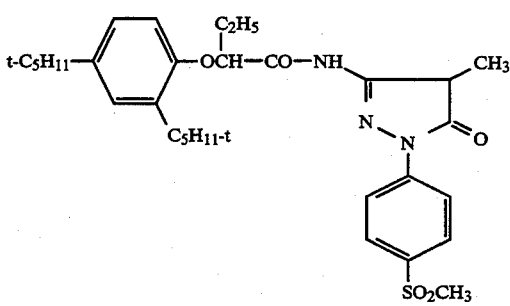

W-4

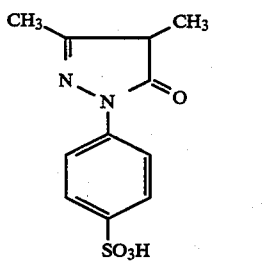

W-5

DIR couplers which release development inhibitors of the azole series, e.g. triazoles and benzotriazoles, are described in DE-A-24 14 006, 26 10 546, 26 59 417, 27 54 281, 28 42 063, 36 26 219, 36 30 564, 36 36 824 and 36 44 416. Further advantages for colour reproduction, i.e. colour separation and colour purity, and for rendering of detail, i.e. sharpness and graininess, may be achieved with DIR couplers which, for example, do not release the development inhibitor directly as a result of coupling with an oxidized colour developer but only after a certain further secondary reaction which is brought about, for example, by means of a time control group. Examples of these are described in DE-A-28 55 697, 32 99 671, 38 18 231 and 35 18 797, EP-A-0 157 146 and 0

204 175, U.S. Pat. Nos. 4,146,396 and 4,438,393 and GB-A-2 072 363.

DAR and FAR couplers which split off a development accelerator or a fogging agent are particularly suitable for increasing the sensitivity, contrast and maximum density. Compounds of this type are described, for example, in DE-A-25 34 466, 32 09 110 33 33 355, 34 10 616, 34 29 545 and 34 41 823, in EP-A-0 089 834, 0 110 511, 0 118 087 and 0 147 565 and in U.S. Pat. Nos. 4,618,572 and 4,656,123.

For an example for the use of BAR couplers (Bleach Accelerator Releasing Coupler), see EP-A-193 389.

It may be advantageous to modify the action of a photographically active group released from a coupler by bringing about an intermolecular reaction of this group with another group after it has been released, as described in DE-A-35 06 805.

The removable group may also be a ballast group so that the reaction with colour developer oxidation products gives rise to coupling products which are diffusible or at least have a weak or limited mobility (U.S. Pat. No. 4,420,556).

The material may also contain compounds which are not couplers but are capable of releasing, for example, a development inhibitor, a development accelerator, a bleaching accelerator, a developer, a silver halide solvent, a lubricant or an antifoggant. Examples of these compounds include so-called DIR hydroquinones and other compounds as described, for example, in U.S. Pat. Nos. 4,636,546, 4,345,024 and 4,684,604, in DE-A-31 45 640, 25 15 213 and 24 47 079 and in EP-A-198 438. These compounds fulfil the same function as DIR, DAR or FAR couplers except that they do not form coupling products.

High molecular weight colour couplers are described for example, in DE-C-1 297 417, DE-A-24 07 569, DE-A-31 48 125, DE-A-32 17 200, DE-A-33 20 079, DE-A-33 24 932, DE-A-33 31 743, DE-A-33 40 376, EP-A-27 284 and U.S. Pat. No. 4,080,211. The high molecular weight colour couplers are generally prepared by the polymerisation of ethylenically unsaturated monomeric colour couplers but they may also be obtained by polyaddition or polycondensation.

The incorporation of couplers or other compounds in silver halide emulsion layers may be carried out by first preparing a solution, dispersion or emulsion of the particular compound and then adding this to the casting solution for the given layer. The choice of suitable solvents or dispersing agents depends on the solubility of the compound.

Methods of grinding for introducing compounds which are substantially insoluble in water are described, for example, in DE-A-26 09 741 and DE-A-26 09 742.

Hydrophobic compounds may also be introduced into the casting solution by means of high boiling solvents, so-called oil formers. Suitable methods are described, for example, in U.S. Pat. Nos. 2,322,027, 2,801,170, 2,801,171 and EP-A-0 043 037. Suitable oil formers for the magenta couplers according to the invention are described, for example, in DE-A-39 18 547.

So-called polymeric oil formers, which may be oligomeric or polymeric, may be used instead of the high boiling solvents.

The compounds may also be introduced into the casting solution in the form of charged latices; see, for example, DE-A-25 41 230, DE-A-25 41 274, DE-A-28 35 856, EP-A-0 014 921, EP-A-0 069 671, EP-A-0 130 115 and U.S. Pat. No. 4,291,113.

Diffusion-fast incorporation of anionic water-soluble compounds (e.g. dyes) may also be carried out by means of cationic polymers, so-called mordant polymers.

Examples of suitable oil formers include the following: Phthalic acid alkyl esters, phosphonic acid esters, phosphoric acid esters, citric acid esters, benzoic acid esters, amides, fatty acid esters, trimesic acid esters, alcohols, phenols, aniline derivatives and hydrocarbons.

The following are specific examples of suitable oil formers:

Dibutyl phthalate, dicyclohexyl phthalate, di-2-ethylhexyl phthalate, decyl phthalate, triphenyl phosphate, tricresyl phosphate, 2-ethylhexyldiphenyl phosphate, tricyclohexyl phosphate, tri-2-ethylhexyl phosphate, tridecyl phosphate, tributoxyethyl phosphate, trichloropropyl phosphate, di-2-ethylhexylphenyl phosphate, 2-ethylhexyl benzoate, dodecyl benzoate, 2-ethylhexyl-p-hydroxybenzoate, diethyl-dodecanamide, N-tetradecyl pyrrolidone, isostearyl alcohol, 2,4-di-t-amylphenol, dioctyl acetate, glycerol tributyrate, isostearyl lactate, trioctyl citrate, N,N-dibutyl-2-butoxy-5-t-octylaniline, paraffin, dodecylbenzene and diisopropyl naphthalene.

Each of the differently sensitized light sensitive layers may consist of a single layer or comprise two or more silver halide emulsion layers (DE-C-1 121 470). Red sensitive silver halide emulsion layers are frequently arranged closer to the layer support than green sensitive silver halide emulsion layers and these in turn are generally closer to the support than blue sensitive layers, and a light insensitive yellow filter layer is generally placed between the green sensitive layers and the blue sensitive layers.

If the green or red sensitive layers have a sufficiently low intrinsic sensitivity, the yellow filter layer may be omitted and other layer arrangements chosen in which, for example, the blue sensitive layers are arranged closest to the support, followed by the red sensitive and finally the green sensitive layers.

The light insensitive interlayers generally placed between layers differing in their spectral sensitivity may contain substances which prevent unwanted diffusion of developer oxidation products from one light sensitive layer into another light sensitive layer which has a different spectral sensitization.

Suitable agents of this kind, also known as scavengers or EOP acceptors, are described in Research Disclosure 7643 (December 1978), Chapter VII, 3.7842 (February 1979) and 18716 (November 1979), page 650, and in EP-A-0 069 070, 0 098 072, 0 124 877 and 0 125 522.

The following are examples of particularly suitable compounds:

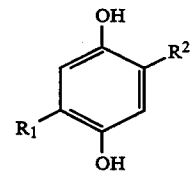

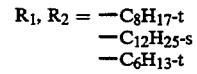

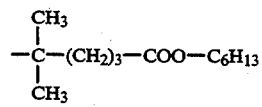

—$C_8H_{17}$-s

—$C_{15}H_{31}$

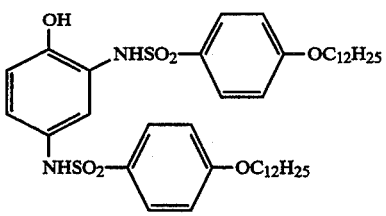

If the photographic material contains several partial layers of the same spectral sensitization, these may differ from one another in their composition, in particular in the type and quantity of the silver halide grains. The partial layer which has the higher sensitivity is generally arranged further away from the support than the partial layer of lower sensitivity. Partial layers having the same spectral sensitization may be arranged adjacent to one another or they may be separated by other layers, e.g. by layers having a different spectral sensitization Thus for example, all highly sensitive layers may be combined in a layer packet and all low sensitivity layers in another packet (DE-A-t9 58 709, DE-A-25 30 645, DE-A-26 22 922).

The photographic material may also contain UV light absorbent compounds, white toners, spacers, filter dyes, formalin acceptors, light protective agents, antioxidants, $D_{min}$ dyes, additives for improving the stabilization of the dyes, couplers and whites and additives for reducing the colour fog, plasticizers (latices), biocides and others.

UV Light absorbent compounds should on the one hand protect the image dyes against bleaching by daylight which is rich in UV light and on the other hand act as filter dyes to absorb the UV light present in daylight when exposure is carried out and thus improve the colour reproduction of a film. Compounds differing in structure are normally used for the two different functions. Examples include aryl substituted benzotriazole compounds (U.S. Pat. No. 3,533,794), 4-thiazolidone compounds (U.S. Pat. Nos. 3,314,794 and 3 352 681), benzophenone compounds (JP-A-2784/71), cinnamic acid ester compounds (U.S. Pat. Nos. 3,705,805 and 3,707,375), butadiene compounds (U.S. Pat. No. 4,045,229) and benzoxazole compounds (U.S. Pat. No. 3,700,455).

The following are examples of particularly suitable compounds:

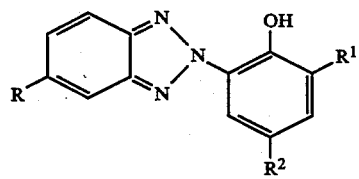

UV-1  R, $R^1$ = H; $R^2$ = —$C_4H_9$-t
UV-2  R = H; $R^1$, $R^2$ = —$C_4H_9$-t
UV-3  R = H; $R^1$, $R^2$ = —$C_5H_{11}$-t
UV-4  R = H; $R^1$ = —$C_4H_9$-s; $R^2$ = —$C_4H_9$-t
UV-5  R = Cl; $R^1$ = —$C_4H_9$-t; $R^2$ = —$C_4H_9$-s
UV-6  R = Cl; $R^1$ = $R^2$ = —$C_4H_9$-t
UV-7  R = Cl; $R^1$ = —$C_4H_9$-t; $R^2$ = —$CH_2$—$CH_2$—$COOC_8H_{17}$
UV-8  R = H; R = —$C_{12}H_{25}$-i; $R^2$ = —$CH_3$

UV-9  R, $R^1$, $R^2$ = —$C_4H_9$-t

UV-10 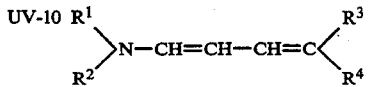

UV-11  $R^1$, $R^2$ = —$C_6H_{13}$-n; $R^3$, $R^4$ = —CN

UV-12  $R^1$, $R^2$ = —$C_2H_5$; $R^3$ = 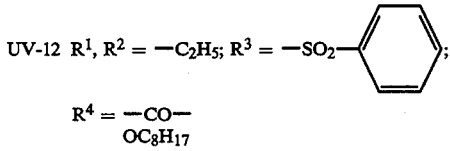

$R^4$ = —CO—$OC_8H_{17}$

UV-13  $R^1$, $R^2$ = —$C_2H_5$; $R^3$ = 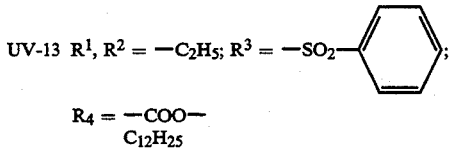

$R_4$ = —COO—$C_{12}H_{25}$

UV-14  $R^1$, $R^2$ = —$CH_2$=CH—$CH_2$; $R^3$, $R^4$ = —CN

UV-15 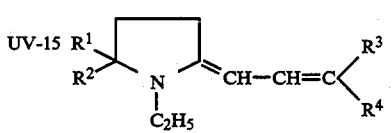

UV-16  $R^1$, $R^2$ = H; $R^3$ = —CN; $R^4$ = —CO—$NHC_{12}H_{25}$
UV-17  $R^1$, $R^2$ = —$CH_3$; $R^3$ = —CN; $R^4$ = —CO—$NHC_{12}H_{25}$

UV-18 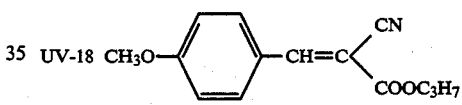

Couplers which absorb ultraviolet (such as cyan couplers of the α-naphthol series) and ultraviolet absorbent polymers may also be used. These ultraviolet absorbents may be fixed in a particular layer by mordants.

Filter dyes suitable for visible light include oxonole dyes, hemi-oxonole dyes, styryl dyes, merocyanine dyes, cyanine dyes and azo dyes. Among these, oxonole dyes, hemi-oxonole dyes and merocyanine dyes are particularly advantageous.

Suitable white toners are described, or example, in Research Disclosure 17643 (December 1978), Chapter V, in U.S. Pat. Nos. 2,632,701 and 3,269,840 and in GB-A-852 075 and 1 319 763.

Certain layers of binders, in particular those furthest removed from the support but occasionally also interlayers, especially if they are furthest away from the support during preparation of the material, may contain photographically inert particles of an inorganic or organic nature, e.g. as matting agents or as spacers (DE-A-33 31 542, DE-A-34 24 893 and Research Disclosure 17643 (December 1978) , Chapter XVI) , The mean particle diameter of the spacers is in particular in the range of from 0.2 to 10 μm. The spacers are insoluble in water and may be insoluble or soluble in alkalies. Those which are soluble in alkalies are generally removed from the photographic material by the alkaline development bath. Examples of suitable polymers include polymethyl methacrylate, copolymers of acrylic acid and methyl methacrylate and hydroxypropyl methyl cellulose hexahydrophthalate.

Additives for improving the stability of the dyes, couplers and whites and for reducing the colour fog (Research Disclosure 17643 (December 1978), Chapter VII) may belong to the following classes of chemical compounds: Hydroquinones, 6-hydroxychromans, 5-hydroxycoumarans, spirochromans, spiroindans, p-alkoxyphenols, sterically hindered phenols, gallic acid derivatives, methylene dioxybenzenes, aminophenols, sterically hindered amines, derivatives containing esterified or etherified phenolic hydroxyl groups, and metal complexes.

Compounds containing both a sterically hindered amine partial structure and a sterically hindered phenol partial structure in one and the same molecule (U.S. Pat. No. 4,268,593) are particularly effective in preventing any impairment of yellow colour images due to the development of heat, moisture or light. Spiroindans (JP-A-159 644/81) and chromans substituted by hydroqinone diethers or monoethers (JP-A-89 835/80) are particularly effective in preventing any impairment of magenta colour images, in particular impairment due to the action of light.

The following are examples particularly suitable compounds:

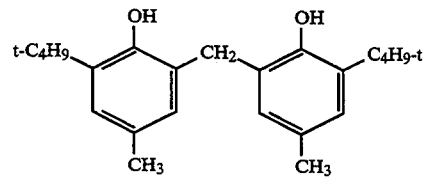

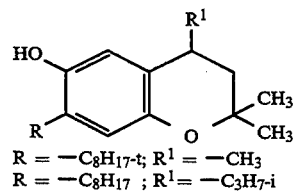

R = —C$_8$H$_{17}$-t; R$^1$ = —CH$_3$
R = —C$_8$H$_{17}$ ; R$^1$ = —C$_3$H$_7$-i

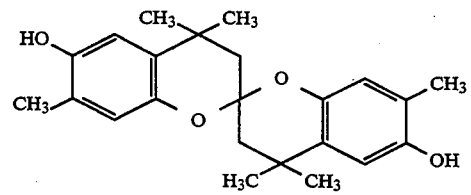

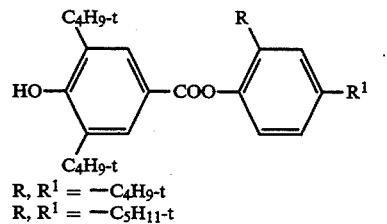

R, R$^1$ = —C$_4$H$_9$-t
R, R$^1$ = —C$_5$H$_{11}$-t

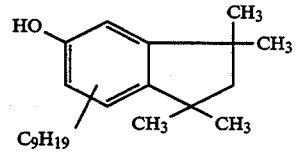

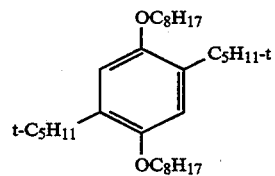

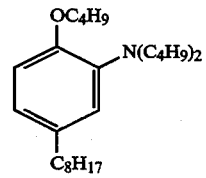

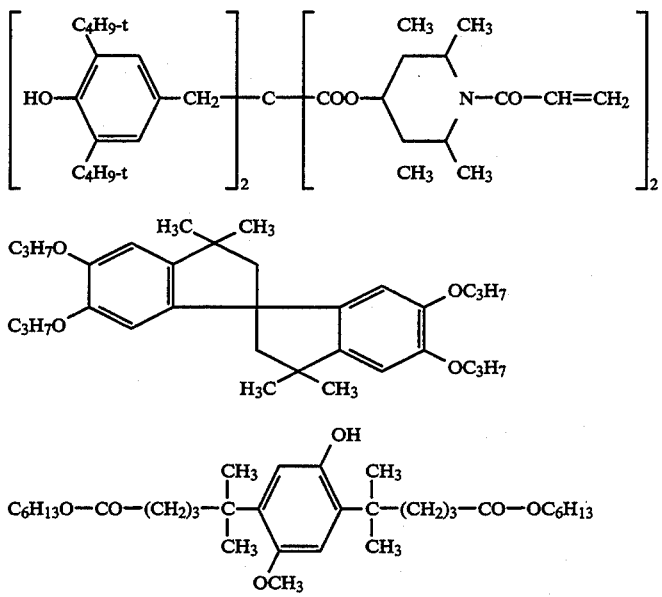

and the compounds listed as EOP acceptors.

Colour photographic recording materials are normally processed by development, bleaching, fixing and washing or by development, bleaching, fixing and stabilization not followed by washing, and bleaching and fixing may be combined in a single process step. Any developer compounds which are capable, in the form of their oxidation product, of reacting with colour couplers to form azomethine or indophenol dyes are suitable colour developers. These include aromatic compounds of the p-phenylenediamine series containing at least one primary amine group, for example: N,N-dialkyl-p-phenylenediamines such as N,N-diethyl-p-phenylenediamine, 1-(N-ethyl-N-methanesulphonamidoethyl)-3-methyl-p-phenylenediamine, 1-(N-ethyl-N-hydroxyethyl)-3-methyl-p-phenylenediamine and 1-(N-ethyl-N-methoxyethyl)-3-methyl-p-phenylenediamine. Other suitable colour developers are described, for example, in J. Amer. Chem. Sec. 73, 3106 (1951) and G. Haist, Modern Photographic Processing, 1979, John Wiley and Sons, New York, page 545 et seq.

Colour development may be followed by an acid stop bath or by washing.

The material is usually bleached and fixed immediately after colour development. The bleaching agents used may be, for example, Fe(III) salts and Fe(III) complex salts such as ferricyanides or dichromates or water-soluble cobalt complexes. Iron(III) complexes of aminopolycarboxylic acids are particularly preferred, in particular e.g. the complexes of ethylene diaminotetracetic acid, propylene diaminotetracetic acid, diethylene triaminopentacetic acid, nitrilotriacetic acid, iminodiacetic acid, N-hydroxyethyl ethylenediaminotriacetic acid and alkyliminodicarboxylic acids and of the corresponding phosphonic acids. Persulphates and peroxides are also suitable bleaching agents, e.g. hydrogen peroxide.

The bleach fixing bath or fixing bath is in most cases followed by washing, which is carried out as a counterflow washing or in several tanks, each with its own water supply.

Favourable results may be obtained by following these steps with a final bath containing little or no formaldehyde.

Washing may be replaced by a stabilizing bath, which is usually carried out in counterflow. This stabilizing bath also functions as final bath when formaldehyde is added.

In colour reversal materials, the process begins with a development with a black-and-white developer whose oxidation product is not capable of reacting with the colour couplers. This is followed by a diffuse second exposure which in turn is followed by development with a colour developer, bleaching and fixing.

EXAMPLES

Example 1

10 g of coupler are dissolved with 10 g of dibutylphthalate and 20 g of ethyl acetate and then emulsified in the usual manner in 100 g of a 10% gelatine solution containing 0.5% of dodecylbenzene sulphonate. The ethyl acetate is then evaporated off.

The emulsion obtained is added to a blue-sensitized silver chloride emulsion so that the mixture then contains 1.3 g of coupler per g of $AgNO_3$.

After the addition of a wetting agent, the casting solution is applied to a polyethylene coated paper with 0.55 g of $AgNO_3/m^2$. This solution is then covered with a gelatine protective layer containing 0.8 g of gelatine/$m^2$.

A hardening layer of 400 mg of gelatine and 400 mg of instant hardener [CAS Reg.-No. 65 411-60-1] is poured on this cast layer. The combination of layers is dried at 50° to 60° C. After drying, the paper is exposed to the light from a 3/2 step wedge behind a blue filter and processed as follows:

| a) | Colour developer - 45 s - 35° C. | |
|---|---|---|
| | Triethanolamine | 9.0 g |
| | N,N-diethylhydroxylamine | 6.0 g |
| | Diethylene glycol | 0.05 g |
| | 3-Methyl-4-amino-N-ethyl-N-methane-sulphonamidoethyl-aniline sulphate | 6.0 g |
| | Potassium sulphite | 0.2 g |

| | |
|---|---|
| Triethylene glycol | 0.05 g |
| Potassium carbonate | 22.0 g |
| Potassium hydroxide | 0.4 g |
| Disodium salt of ethylene diamino- tetracetic acid | 2.2 g |
| made up with water to 1,000 ml; pH 9.2. | | b) Bleach fixing bath - 45 s - 35° C.

| | |
|---|---|
| Ammonium thiosulphate | 75 g |
| Sodium hydrogen sulphite | 13.5 g |
| Ammonium acetate | 2.0 g |
| Ethylenediaminotetracetic acid (iron-ammonium salt) | 57.0 g |
| Ammonia 25% | 9.5 g |
| Acetic acid | 9.0 g |
| made up with water to 1,000 ml; pH 5.5. | | c) Washing - 2 min - 33° C.

The wedges thus obtained are irradiated with a Xeno test apparatus for various lengths of time.

The residual densities left after various initial densities (0.5; 1.0; 1.5; $D_{max}$) are then measured and expressed in terms of % regression, based on the initial densities (Table 1).

Table 1 shows that the couplers according to the invention suffer less colour density loss and have distinctly higher residual densities after irradiation.

The following comparison couplers were used:

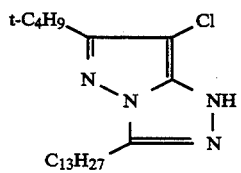

CC-1

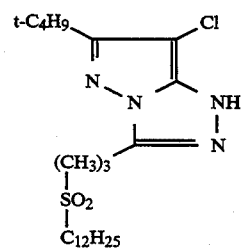

CC-2

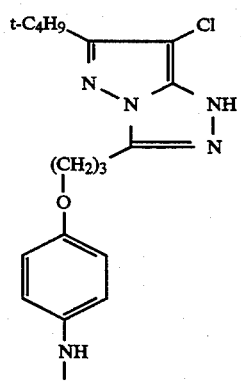

CC-3

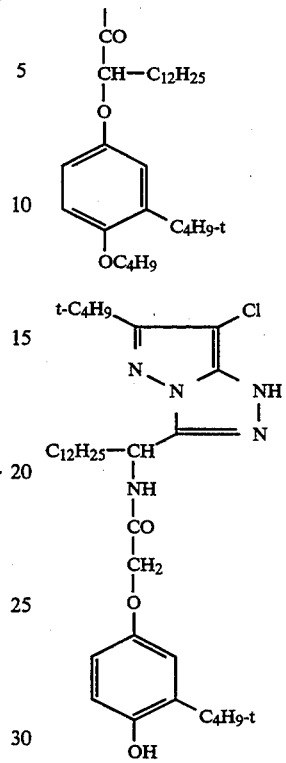

CC-4

TABLE 1

| Coup-ler | 2.4 × 10⁶ lux · h | | | | 4.8 × 10⁶ lux · h | | | | 14.4 × 10⁶ lux · h | | | |
|---|---|---|---|---|---|---|---|---|---|---|---|---|
| | Density | | | | | | | | | | | |
| | 0.5 | 1.0 | 1.5 | $D_{max}$ | 0.5 | 1.0 | 1.5 | $D_{max}$ | 0.5 | 1.0 | 1.5 | $D_{max}$ |
| CC-1 | 66 | 60 | 33 | 10 | 72 | 50 | 44 | 22 | 88 | 86 | 70 | 68 |
| CC-2 | 55 | 50 | 26 | 9 | 68 | 48 | 45 | 20 | 84 | 80 | 76 | 70 |
| CC-3 | 60 | 40 | 28 | 17 | 82 | 76 | 44 | 30 | 92 | 81 | 75 | 68 |
| CC-4 | 62 | 48 | 30 | 20 | 71 | 63 | 50 | 35 | 82 | 80 | 72 | 69 |
| M-1 | 35 | 30 | 14 | 5 | 44 | 34 | 30 | 20 | 50 | 45 | 35 | 38 |
| M-5 | 40 | 35 | 17 | 12 | 45 | 37 | 22 | 19 | 47 | 42 | 38 | 35 |
| M-12 | 33 | 27 | 16 | 5 | 40 | 30 | 21 | 12 | 51 | 47 | 37 | 30 |
| M-26 | 33 | 30 | 17 | 6 | 38 | 36 | 30 | 14 | 48 | 45 | 42 | 28 |

Example 2

A colour photographic recording material suitable for rapid processing was prepared by applying the following layers in the given sequence to a layer support of paper which was coated with polyethylene on both sides. The quantities given are based in each case on 1 m². The quantities of silver halide applied are given in terms of the corresponding quantities of AgNO₃

| Layer arrangement 1 (Comparison) | |
|---|---|
| Layer 1: | (Subbing layer) 0.2 g gelatine |
| Layer 2: | (blue sensitive layer) blue sensitive silver halide emulsion (99.5 mol-% chloride, 0.5 mol-% bromide, mean grain diameter 0.8 μm) of 0.63 g of AgNO₃ with 1.38 g gelatine 0.95 g yellow coupler XY-1 0.2 g white coupler XW-1 0.29 g tricresyl phosphate (TCP) |
| Layer 3: | (protective layer) 1.1 g gelatine 0.06 g 2,5-dioctylhydroquinone |

-continued

Layer arrangement 1 (Comparison)

| | |
|---|---|
| Layer 4: | 0.06 g dibutyl phthalate (DBP) (green sensitive layer) green sensitized silver halide emulsion (99.5 mol-% chloride, 0.5 mol-% bromide, mean grain diameter 0.6 μm) of 0.45 g AgNO₃ with 1.08 g gelatine 0.41 g magenta coupler XM-1 0.03 g 2,5-dioctylhydroquinone 0.34 g DBP 0.04 g TCP |
| Layer 5: | (red sensitive layer) red sensitized silver halide emulsion (99.5 mol-% chloride, 0.5 mol-% bromide, mean grain diameter 0.5 μm) of 0.30 g AgNO₃ with 0.75 g gelatine 0.36 g cyan coupler XC-1 0.36 g TCP |
| Layer 6: | (protective layer) 0.9 g gelatine 0.3 g hardener carbamoyl pyridinium salt (CAS Reg. No. 65411-60-1) |

The following compounds were used in layer arrangement 1:

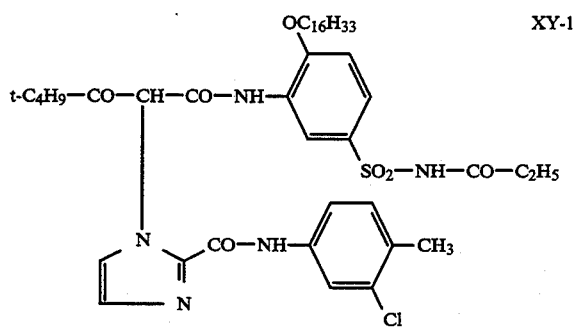

XY-1

XM-1

XC-1

XW-1

The material thus prepared is referred to as Sample 1 comparison). Further samples 2–8 were prepared analogously, using comparison couplers CC-2, CC-1 and CC-5 and the couplers according to the invention M-I, M-12, M-4 and M-19. In these samples, comparison coupler XM-1 was replaced by the above-mentioned couplers as shown in Table 2. Samples 1–4 serve for comparison; samples 5–8 are according to the invention.

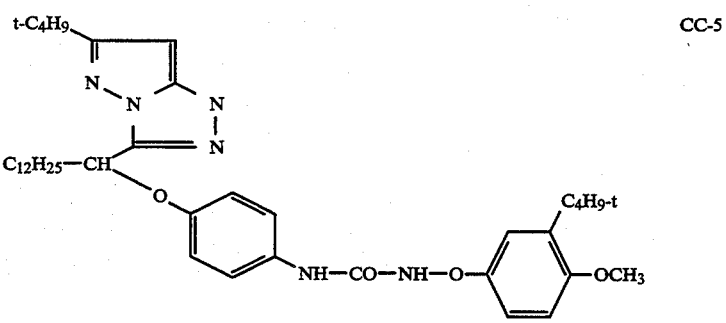

CC-5

Samples 1 to 8 were processed as described in Example 1 after exposure through a 3/2 step wedge and then irradiated in a Xeno test apparatus for various lengths of time. The results (percentage colour density regression) are shown in Table 2.

TABLE 2

| Sample | Coupler | 2.4 × 10⁶ lux · h | | | | 4.8 × 10⁶ lux · h | | | | 9.6 × 10⁶ lux · h | | | |
|---|---|---|---|---|---|---|---|---|---|---|---|---|---|
| | | Density | | | | | | | | | | | |
| | | 0.5 | 1.0 | 1.5 | $D_{max}$ | 0.5 | 1.0 | 1.5 | $D_{max}$ | 0.5 | 1.0 | 1.5 | $D_{max}$ |
| 1 | XM-1 | 55 | 19 | 20 | 10 | 60 | 25 | 30 | 18 | 85 | 78 | 70 | 69 |
| 2 | CC-2 | 62 | 28 | 22 | 8 | 81 | 78 | 68 | 35 | 90 | 85 | 84 | 79 |
| 3 | CC-1 | 75 | 51 | 33 | 20 | 86 | 87 | 80 | 66 | 95 | 90 | 88 | 91 |
| 4 | CC-5 | 58 | 35 | 10 | 6 | 76 | 35 | 28 | 19 | 87 | 72 | 73 | 69 |
| 5 | M-1 | 35 | 24 | 14 | 5 | 41 | 20 | 18 | 10 | 60 | 44 | 25 | 17 |
| 6 | M-12 | 30 | 20 | 9 | 3 | 39 | 22 | 20 | 10 | 54 | 35 | 24 | 19 |
| 7 | M-4 | 39 | 27 | 18 | 14 | 42 | 21 | 15 | 11 | 63 | 42 | 21 | 12 |
| 8 | M-19 | 28 | 15 | 9 | 5 | 38 | 24 | 19 | 9 | 58 | 29 | 22 | 18 |

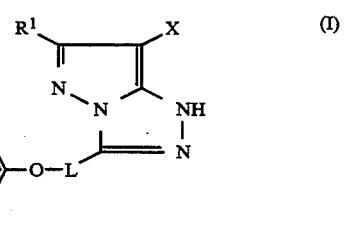

It is clear from Table 2 that the compounds according to the invention undergo substantially less bleaching when irradiated in the Xeno test. In addition, comparison coupler XH-1 shows distinctly inferior colour reproduction due to increased side density in the blue spectral region.

The values shown in Table 3 (percentage colour density regression) result when an additional layer 4a of the following composition is placed between layers 4 and 5:

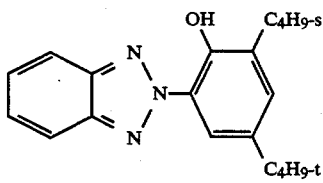

and an additional layer 5a of the following composition is placed between the 5th and 6th layer:

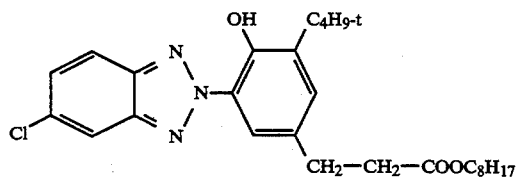

| | 14.4 · 10⁶ lux · h | | | |
|---|---|---|---|---|
| | Density | | | |
| Sample | 0.5 | 1.0 | 1.5 | Dmax |
| 1 | 64 | 58 | 49 | 40 |
| 2 | 76 | 83 | 74 | 68 |
| 3 | 83 | 75 | 68 | 57 |
| 4 | 80 | 69 | 65 | 62 |
| 5 | 40 | 38 | 35 | 19 |
| 6 | 38 | 35 | 30 | 25 |
| 7 | 46 | 41 | 38 | 29 |
| 8 | 37 | 39 | 29 | 21 |

I claim:

1. A color photographic recording material containing at least one silver halide emulsion layer arranged on a layer support and at least one non-diffusible magenta coupler of the pyrazolo[3,2-c]-1,2,4-triazole series, characterized in that the coupler corresponds to the following general formula I wherein
R¹ denotes alkyl;
R² denotes an alkyl group substituted by a member selected from the group consisting of OH, alkoxy, COOH and aryl;
R³ denotes alkyl or aryl;
t stands for 0 to 4; or R² and R³ together denote a group for completing a 5-, 6- or 7- membered, optionally substituted ring;
L denotes a straight chain or branched alkylene group optionally interrupted by O;
X denotes H or a group which can be split off in the process of colour development.

2. A recording material according to claim 1, characterised in that an alkylene group denoted by L in formula I contains up to 20 carbon atoms, up to 8 carbon atoms of which are in the main chain between the coupler portion and the hydroquinone portion.

3. A recording material according to claim 2, characterised in that the alkylene group denoted by L in formula I contains at least 2 carbon atoms in the main chain between the coupler portion and the hydroquinone portion.

4. A recording material according to claim 1, characterised in that the alkyl group denoted by R³ is tertiary butyl.

5. A recording material according to claim 1, characterised in that the alkyl group denoted by R¹ is isopropyl or tertiary butyl.

6. A recording material according to claim 1, characterised in that X in formula I stands for chlorine or for a group which imparts no colour to the coupler and is attached at the coupling position by way of an oxygen atom, a sulphur atom or a nitrogen atom.

7. A recording material according to claim 1, characterised in that the silver halide in the silver halide emulsion layers consists to an extent of at least 98 mol- % of silver chloride.

8. A recording material according to claim 7, characterised in that the layer support is a light reflecting layer support.

9. A recording material according to claim 1, characterised in that a phenolic cyan coupler which carries a ballasted acylamino group in the 2-position and an ethyl group in the 5-position is contained in at least one of the light sensitive layers.

10. A recording material according to claim 1, characterised in that a pivaloyl acetanilide yellow coupler is contained in at least one of the light sensitive layers.

* * * * *